US010145832B2

(12) United States Patent
Fukuzawa et al.

(10) Patent No.: US 10,145,832 B2
(45) Date of Patent: Dec. 4, 2018

(54) REMOTE MONITORING DEVICE FOR BALLAST WATER TREATMENT SYSTEM AND REMOTE MONITORING METHOD

(71) Applicant: KURITA WATER INDUSTRIES LTD., Tokyo (JP)

(72) Inventors: Kotaro Fukuzawa, Tokyo (JP); Tetsuo Koga, Tokyo (JP); Kazuki Hayashi, Tokyo (JP); Tetsuro Fukase, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 694 days.

(21) Appl. No.: 14/388,396

(22) PCT Filed: Feb. 27, 2013

(86) PCT No.: PCT/JP2013/055072
§ 371 (c)(1),
(2) Date: Sep. 26, 2014

(87) PCT Pub. No.: WO2013/146033
PCT Pub. Date: Oct. 3, 2013

(65) Prior Publication Data
US 2015/0081227 A1    Mar. 19, 2015

(30) Foreign Application Priority Data

Mar. 28, 2012    (JP) ................... 2012-075040

(51) Int. Cl.
*G01N 33/18*    (2006.01)
*G01N 11/00*    (2006.01)
(Continued)

(52) U.S. Cl.
CPC .......... *G01N 33/1826* (2013.01); *B63J 4/002* (2013.01); *C02F 1/008* (2013.01);
(Continued)

(58) Field of Classification Search
CPC .......... G01N 33/1826; G01N 33/1886; G01N 27/06; G01N 21/00; C02F 1/008; C02F 2209/22; C02F 2103/008; C02F 2303/04
See application file for complete search history.

(56) References Cited

U.S. PATENT DOCUMENTS 6,444,119 B1 * 9/2002 Mains, Jr. .......... B01D 17/0205
                                                                210/130
6,826,514 B1 * 11/2004 Antico .................... G01D 9/005
                                                                340/539.1
(Continued)

FOREIGN PATENT DOCUMENTS

JP    2007-526158 A    9/2007
JP    2008-100157 A    5/2008
(Continued)

OTHER PUBLICATIONS

International Search Report of the International Searching Authority dated Jun. 4, 2013 for the corresponding international application No. PCT/JP2013/055072 (and English translation).

*Primary Examiner* — John Breene
*Assistant Examiner* — Mohammad Islam
(74) *Attorney, Agent, or Firm* — Posz Law Group, PLC

(57) ABSTRACT

A state of a ballast water treatment system of a ship detected by a variety of sensors is monitored by transmitting it to a control means provided with a data storage/transmission means. The control means transmits from a satellite communication means to a satellite communication means on the receiving side via a communication satellite, and a host computer receives it. The host computer analyzes and monitors information from the various sensors S1 to S6 and sends back an optimal operation state, which is received by the satellite communication means on the ship side via the communication satellite, and the control means maintains an operation of the ballast water treatment system based on (Continued)

instructions from the host computer. According to the remote monitoring device for a ballast water treatment system as above, the ballast water treatment system can be monitored and controlled from remote.

13 Claims, 1 Drawing Sheet

(51) Int. Cl.
| | | |
|---|---|---|
| *G01N 27/06* | (2006.01) | |
| *G01N 21/00* | (2006.01) | |
| *B63J 4/00* | (2006.01) | |
| *G01N 27/26* | (2006.01) | |
| *C02F 1/00* | (2006.01) | |
| C02F 1/76 | (2006.01) | |
| C02F 103/00 | (2006.01) | |

(52) U.S. Cl.
CPC ............ *G01N 11/00* (2013.01); *G01N 21/00* (2013.01); *G01N 27/06* (2013.01); *G01N 27/26* (2013.01); *G01N 33/1886* (2013.01); *C02F 1/76* (2013.01); *C02F 2103/008* (2013.01); *C02F 2209/008* (2013.01); *C02F 2209/04* (2013.01); *C02F 2209/22* (2013.01); *C02F 2303/04* (2013.01)

(56) References Cited

U.S. PATENT DOCUMENTS

| | | | |
|---|---|---|---|
| 2003/0176971 A1* | 9/2003 | Daniels | B63J 99/00 702/2 |
| 2005/0016933 A1* | 1/2005 | Perlich | C02F 1/763 210/754 |
| 2006/0027507 A1* | 2/2006 | van Leeuwen | B63B 13/00 210/760 |
| 2008/0277354 A1* | 11/2008 | Baerheim | B63J 4/002 210/750 |
| 2010/0072144 A1* | 3/2010 | Osakabe | C02F 1/70 210/752 |
| 2010/0116647 A1* | 5/2010 | Kornmuller | B63J 4/004 204/228.1 |
| 2011/0114569 A1* | 5/2011 | Kim | C02F 1/4674 210/739 |
| 2013/0284678 A1* | 10/2013 | Daly | C02F 1/008 210/722 |

FOREIGN PATENT DOCUMENTS

| | | |
|---|---|---|
| JP | 2010-042331 A | 2/2010 |
| JP | 2012-007969 A | 1/2012 |
| JP | 2012-008115 A | 1/2012 |
| JP | 2012-056529 A | 3/2012 |
| WO | 2004/113472 A3 | 12/2004 |

* cited by examiner

REMOTE MONITORING DEVICE FOR BALLAST WATER TREATMENT SYSTEM AND REMOTE MONITORING METHOD

CROSS REFERENCE TO RELATED APPLICATIONS

This application is a U.S. national stage application of PCT/JP2013/055072 filed on Feb. 27, 2013, and claims priority to, and incorporates by reference, Japanese Patent Application No. 2012-075040 filed on Mar. 28, 2012.

TECHNICAL FIELD

The present invention relates to a remote monitoring device for a ships' ballast water treatment system and a remote monitoring method for a ballast water treatment system using the remote monitoring device.

BACKGROUND ART

Ships, specially cargo ships, are generally designed considering to include weight of loaded cargos, etc., therefore, a ship in a state of loaded with no or few cargos takes in sea water, etc. at a port before departure to keep balance of the ship for the necessity of securing the propeller immersion depth and navigational safety, etc. during no cargo. The water used as ballast is called ships' ballast water. The ships' ballast water is sea water, etc. loaded to a ballast tank at a port when departing the port with no cargo, while the ships' ballast water is discharged when loading cargos at a port.

When filling and discharging ships' ballast water to and from ships moving between loading ports and unloading ports of different environments, there is a concern of adversely affecting ecosystems of coasts by difference of microorganisms included in the ships' ballast water between the loading port and unloading port. Therefore, at the international convention for the management of ships' ballast water of ships, the international treaty for the Control and Management of Ships' Ballast Water and Sediments of ships was adopted in February of 2004 and a treatment of ships' ballast water became obliged.

The standard of ships' ballast water treatment established by the International Maritime Organization (IMO) is that the number of living organisms of 50 μm or greater (mainly zooplankton) included in ships' ballast water to be discharged from ships is less than 10 per 1 $m^3$, the number of living organisms of 10 μm or greater but smaller than 50 μm (mainly phytoplankton) is less than 10 in 1 ml, the number of cholera is less than 1 cfu per 100 ml, the number of *Escherichia coli* is less than 250 cfu per 100 ml, and the number of Intestinal Enterococci is less than 100 cfu per 100 ml.

To satisfy the treatment standard of ballast water as above, as a ballast water treatment system, systems combining a storage device or a shipboard generation device of an active substance of, for example, chlorine-based or oxygen-based (bactericidal agent), a device for adding the active substance to ballast water, and a neutralizer adding device for neutralizing the active substance remaining in ballast water when discharging the ballast water are often adopted.

Such a ballast water treatment system has to be operated reliably by confirming that the ballast water treatment system operates normally during staying at a port, and it is also necessary that a resupply of chemicals and monitoring of an operating state (maintenance check) are done after adjusting the state according to the circumstances of the port in some cases. Particularly, since active substances as a bactericidal agent to be used in the ballast water treatment system are often hazardous to human body, ships and the environment, the maintenance check and other operations of the ballast water treatment system have to be done after a safety check of at least a normal level in a state of wearing a protective equipment, therefore, it takes a long time. Furthermore, it is necessary to make sure that water to be discharged has a safe water quality of not negatively affecting the environment.

DISCLOSURE OF THE INVENTION

Problems to be Solved by the Invention

On the other hand, generally, time staying at a port is normally set as short as possible in terms of an efficiency of ship's operations and costs, etc. In order to carry out many operations including the dangerous operation as explained above safely and efficiently during the short stop, it is necessary to perceive a state of the ballast water treatment system in advance and to set up necessary preparations at the port of call.

However, monitoring of ballast water treatment system of the related art has been only carried out on ships, such as a shipboard wheelhouse or through a monitor attached to a device, and there has not been any remote monitoring system for perceiving the state of the ballast water treatment system and setting up necessary preparations at a port of call. Particularly, sodium hypochlorite and other hypochlorite are often used as an active substance, however, sodium hypochlorite is poor in a preserving property and an effective chlorine concentration thereof declines gradually over time, so that it is unfavorable to load a large amount on a ship to travel and it is preferable to load a necessary amount at a port of call.

The present invention has an object thereof to solve the problems above and to provide a remote monitoring device for a ballast water treatment system, by which the ballast water treatment system can be remotely monitored and controlled. Also, the present invention has an object thereof to provide a remote monitoring method for a ballast water treatment system using the remote monitoring device for the ballast water treatment system.

Means to Solve the Problems

To attain the above objects, firstly, the present invention provides a remote monitoring device for a ballast water treatment system provided to a ship, wherein the ballast water treatment system comprises a treatment effect confirmation means, an environment safety monitoring means, a control means, and a data storage/transmission means for treatment effect data and environment safety data connected to the treatment effect confirmation means and the environment safety monitoring means; the data storage/transmission means are connected by wireless with a host computer provided away from the ship; and the host computer monitors a state of the ballast water treatment system by using the control means based on treatment effect data and environment safety data received from the data storage/transmission means and maintains and manages operations of the ballast water treatment system to be proper (Invention 1).

According to the invention (Invention 1), treatment effect data and environment safety data of a ballast water treatment system are connected by wireless to a host computer provided away from the ship via a satellite communication, etc., so that the host computer monitors a state of the ballast water treatment system and perceives the state. Then, operations of the ballast water treatment system is maintained based on instructions from the host computer, and instructions on provisional work and preparation work in accordance with the state of the ballast water treatment system are given to a port of call side, so that lots of work to be done to the ballast water treatment system after arriving at the port are finished in advance and work relating to the ballast water treatment system can be carried out safely and efficiently during the short stop at the port.

In the invention (Invention 1) above, preferably, the treatment effect confirmation means is one or more kinds selected from a residual oxidant sensor, an ultraviolet sensor, an oxidizing-reducing potentiometer, a dissolved oxygen meter, a level meter of a bactericidal agent tank, a flowmeter of a bactericidal agent, and a flowmeter of an electrolytic device (Invention 2).

According to the invention (Invention 2), by monitoring the ballast water treatment system based on the data, a state of an active substance (bactericidal agent) can be perceived, therefore, an active substance, such as easily-degradable sodium hypochlorite, can be supplied properly by loading a necessary amount for the next travel length at a port of call.

In the invention (Inventions 1 and 2) above, preferably, the environment safety monitoring means is one or more kinds selected from a residual oxidant sensor, an oxidizing-reducing potentiometer, a level meter of a bactericidal-agent neutralizer tank, and a flowmeter of a neutralizer (Invention 3).

According to the invention (Invention 3) above, since a state of a substance, which may be hazardous to environmental safety, can be perceived by monitoring the ballast water treatment system based on the data, it is possible to resupply a necessary amount of neutralizer properly and discharge ballast water safely at a port of call, etc.

Secondly, the present invention provides a remote monitoring method for a ballast water treatment system provided to a ship: wherein treatment effect data and environment safety data obtained by a treatment effect confirmation means and an environment safety monitoring means provided to the ballast water treatment system are transmitted to a data storage/transmission means; the data storage/transmission means transmits by wireless the data to a host computer provided away from the ship; and the host computer monitors from remote a state of the ballast water treatment system by using the control means based on treatment effect data and environment safety data received from the data storage/transmission means and maintains and manages operations of the ballast water treatment system to be proper (Invention 4).

According to the invention (Invention 4), a state of a ballast water treatment system on a ship is perceived by a host computer in advance, operations of the ballast water treatment system are maintained based on instructions from the host computer, instructions for provisional work and preparation work in accordance with the state of the ballast water treatment system are given to the port of call side, and lots of work to be done to the ballast water treatment system after arriving at the port are finished in advance, therefore, work relating to the ballast water treatment system can be carried out safely and efficiently during a short stop at the port.

Effect of the Invention

According to the remote monitoring device for a ballast water treatment system provided to a ship of the present invention, treatment effect data and environment safety data of the ballast water treatment system are received by a host computer provided away from a ship via a satellite communication, etc., so that the host computer monitors and perceives a state of the ballast water treatment system. Then, by maintaining an operation of the ballast water treatment system based on instructions from the host computer, giving instructions on a provisional work and preparation work to the port of call side in accordance with the state of the ballast water treatment system, and finishing in advance lots of work to be done to the ballast water treatment system after reaching the port, it becomes possible to carry out the operation relating to the ballast water treatment system safely and efficiently during the short stop at the port.

MODE(S) FOR CARRYING OUT THE INVENTION

Figure 1:
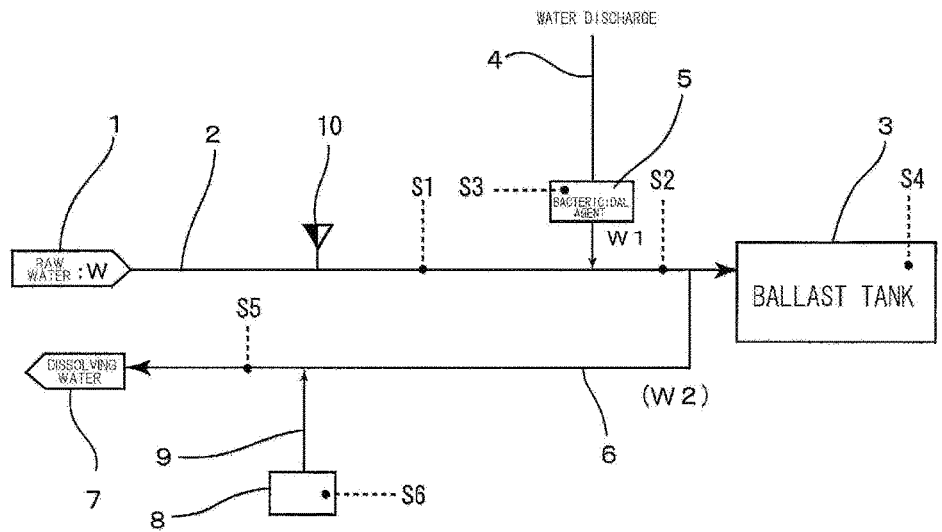
FIG. 1 A schematic diagram showing an example of a ballast water treatment system, wherein the remote monitoring device for a ballast water treatment system according to the present invention can be applied.

Below, an explanation will be made on a remote monitoring device for a ships' ballast water treatment system of the present embodiment with reference to FIG. 1 and FIG. 2. FIG. 1 is a flow chart showing an embodiment of a ballast water treatment system, which can be controlled by the remote monitoring device of the present invention.

In FIG. 1, the ships' ballast water treatment system comprises a water intake portion 1 of raw water W as ballast water, a main line 2 for feeding the raw water W connected to the water intake portion 1, and a ballast tank 3 provided to an end of the main line 2. A not-illustrated liquid feed pump as a water feed means is provided to the middle of the main line 2 and joined with a supply line 4 of a bactericidal agent, which is an active substance. A bactericidal agent tank 5 is provided halfway on the bactericidal agent supply line 4, which is configured to supply dissolving water from an end side so as to discharge bactericidal agent solution W1.

The main line 2 branches halfway to a discharge line 6 and an end thereof is a water discharge portion 7, and a reductant supply tube 9 connected to a neutralizer storage tank 8 is connected halfway on the discharge line 6. Note that 10 indicates an open/close valve for switching between the main line 2 and the discharge line 6.

In the ships' ballast water treatment system as explained above, a first flow sensor S1 is provided on the upstream side of the branched part of the discharge line 6 of the main line 2 and a second flow sensor S2 is provided on the downstream side of the joining point with the bactericidal agent supply line 4, and those sensors are capable of measuring a flow amount of bactericidal agent solution W1 in addition to a flow amount of raw water W. Also, the bactericidal agent tank 5 is provided with a sensor S3 having a level meter and a chlorine sensor, and the ballast tank 3 is provided with a sensor S4 having a residual oxidant (TRO) sensor, oxidation-reduction potentiometer and dissolved oxygen meter. The first flow sensor S1, second flow sensor S2, sensor S3 and sensor S4 compose a treatment effect confirmation means. On the other hand, the discharge line 6 is provided with a sensor S5 having a residual oxidant sensor and oxidation-reduction potentiometer and, furthermore, the neutralizer storage tank 8 is provided with a sensor S6 having a level meter of a neutralizer and a flowmeter of a neutralizer. The sensor S5 and sensor S6 compose an environment safety monitoring means. Note that those sensors are not particularly limited and commercially available ones may be used.

The sensors S1 to S6 are connected to a not shown control system provided with a not shown data storage/transmission means of environment safety data, and the control system conducts basic operation management of the ballast water treatment system and is connected by wireless via satellite communication with the host computer provided away from the ship.

Note that in the ships' ballast water treatment system of the present embodiment, those including sodium hypochlorite as the main component are suitable as an active substance (bactericidal agent) and, furthermore, those blended with phosphate and sodium hydroxide, etc. as needed and adjusted to have a pH of 10 to 13 or so are preferable.

Next, an explanation will be made on a ballast water treatment method for performing an extinction treatment of bacteria and plankton when loading ballast water.

Firstly, when loading raw water (ballast water) W at leaving a port, by driving the liquid feed pump with the open/close valve 10 open, raw water W is fed from the water intake portion 1 to the ballast tank 3 through the main line 2. During this, a bactericidal agent solution W1 is supplied form the bactericidal agent supply line 4 to join the main line 2. By supplying the bactericidal agent solution W1 to the ballast tank 3 in this way, plankton and bacteria in the raw water W can be killed by effective chlorine generated from the bactericidal agent.

Next, an explanation will be made on discharging ballast water when arriving or stopping at a port. When discharging ballast water from the ballast tank 3, the liquid feed pump is driven with the open/close valve 10 closed. As a result, ballast water to be discharged W2 in the ballast tank 3 is discharged from the discharge line 6 through a part of the main line 2.

During this, by supplying a neutralizer from the neutralizer storage tank 8 in accordance with a residual chlorine concentration in the ballast water to be charged W2, it is possible to discharge the ballast water to be discharged W2 in a state safe to the environment. As the neutralizer, sodium sulfite, sodium bisulfite (sodium hydrogensulfite) and sodium thiosulfate, etc. may be preferably used.

Figure 2:
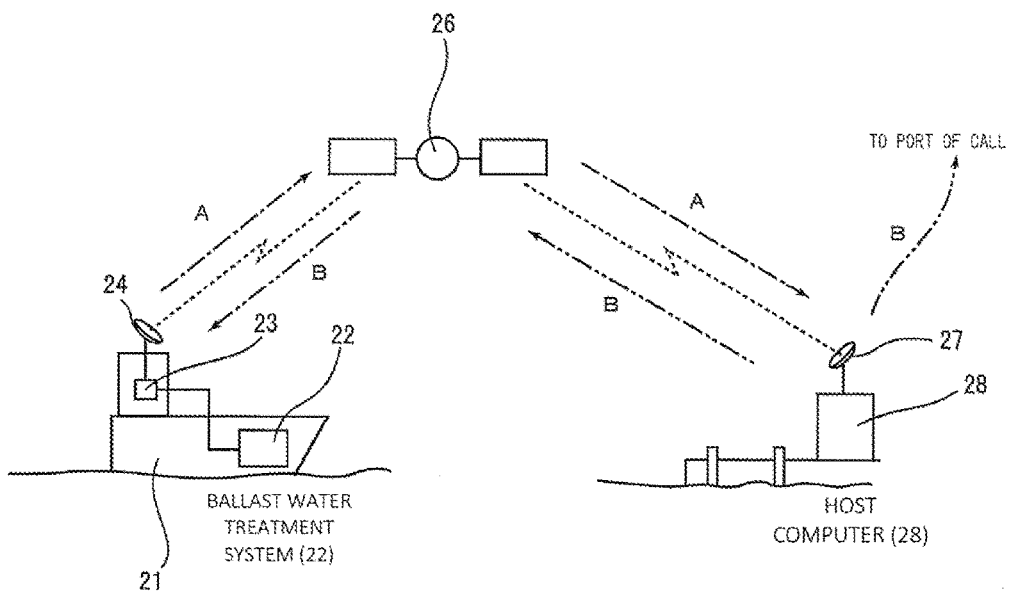
FIG. 2 A schematic diagram showing a remote monitoring device for a ballast water treatment system according to an embodiment of the present invention.

When the ship equipped with the ballast water treatment system as above is out at sea, it is controlled by a remote monitoring device as shown in FIG. 2 in the present embodiment.

In FIG. 2, a ship 21 is provided with a ballast water treatment system 22, a control means 23 having a storage/transmission means of data detected at the variety of sensors S1 to S6 of the ballast water treatment system 22, and a satellite communication means 24 having a transmission function for transmitting data from the variety of sensors S1 to S6 and a receiving function. On the other hand, on the host computer 28 side on the land, a satellite communication means 27 having a transmitting/receiving function is provided, and the control means 23 on the ship 21 and the host computer 28 are connected by wireless via a communication satellite 26.

In the remote monitoring device as above, a state of the ballast water treatment system 22 detected by the variety of sensors S1 to S6 during out at sea is monitored by transmitting to the data storage/transmission means provided to the control means 23. Since the control means 23 is connected by wireless via the communication satellite 26 with the host computer 28, the data is transmitted from the satellite communication means 24 to the satellite communication means 27 on the receiver side via the communication satellite 26 and received on the host computer 28 side (arrows A in FIG. 2).

In the host computer 28, information from the variety of sensors S1 to S6 is analyzed and monitored, and an optimal operation state is sent back. Then, on the ship 21 side, it is received by the satellite communication means 24 via the communication satellite 26 and the control means 23 maintains the operation of the ballast water treatment system 22 based on instructions from the host computer (arrows B in FIG. 2). Furthermore, the host computer 28 instructs provisional work and preparation work to a port of call for stopping in the middle of travel in accordance with the state of the ballast water treatment system 22 (arrows B in FIG. 2). Thereby, by finishing in advance lots of work to be done to the ballast water treatment system 22 after arriving at the port, it becomes possible to carry out work relating to the ballast water treatment system 22 safely and effectively during a short stop at the port.

According to the remote monitoring device for the ballast water treatment system 22 of the present embodiment as explained above, since the ship 21 travels anywhere on the glove, it utilizes the fact that location information, etc. of a ship 21 is connected by wireless via the satellite communication 26 and necessity of resupply of chemicals, such as a bactericidal agent and neutralizer, can be informed in advance, it is not necessary to load those chemicals on the ship 21 and a necessary resupply can be carried out in a structured way when arrived at a port. Also, operation record of the ballast water treatment system 22 can be made automatically. Furthermore, there is an effect that a failure of the ballast water treatment system 22 can be perceived at a port of call in advance through the host computer on the land, so that it can be handled promptly when arrived at the port. Particularly, general-purpose sodium hypochlorite as an active substance (bactericidal agent) is poor at a preserving property and the effective chlorine concentration declines gradually. Therefore, by carrying and refilling a necessary amount immediately before leaving a port, the efficiency can be improved.

The present invention was explained above with reference to the attached drawings, however, the present invention is not limited to the embodiments above and can be modified variously. For example, as a treatment effect confirmation means, an ultraviolet sensor and an ammeter of an electrolytic device, etc. may be also used. Furthermore, the environment safety monitoring means may use an oxidation-reduction potentiometer, etc.

Also, for the treatment effect confirmation means, one or more kinds may be selected for use arbitrarily from a residual oxidant sensor, ultraviolet sensor, oxidation-reduction potentiometer, dissolved oxygen meter, level meter of a bactericidal agent tank, flowmeter of a bactericidal agent, ammeter of an electrolytic device in accordance with the configuration of the ballast water treatment system. Furthermore, for the environmental safety monitoring means, one or more kinds may be selected for use arbitrarily from a residual oxidant sensor, oxidation-reduction potentiometer, level meter of a bactericidal-agent neutralizer tank and flowmeter of neutralizer in accordance with the configuration of the ballast water treatment system.

INDUSTRIAL APPLICABILITY

The remote monitoring device for the ballast water treatment system of the present invention may be suitably used for ships' ballast water treatment of a variety of ships, large-scale ships in particular.

EXPLANATION OF NUMERICAL REFERENCES

21 ... ship
22 ... ballast water treatment system
23 ... control means
24 ... satellite communication means (wireless connection means)
26 ... communication satellite (wireless connection means)
27 ... satellite communication means (wireless connection means)
28 ... host computer
S1 ... first flowmeter (treatment effect confirmation means)
S2 ... second flowmeter (treatment effect confirmation means)
S3 ... sensor (treatment effect confirmation means)
S4 ... sensor (treatment effect confirmation means)
S5 ... sensor (environment safety monitoring means)
S6 ... sensor (environment safety monitoring means)

The invention claimed is:

1. A remote monitoring device for a ballast water treatment system provided to a ship, comprising:
the ballast water treatment system comprises a treatment effect confirmation means, an environment safety monitoring means, a control means, and a data storage/transmission means for treatment effect data and environment safety data connected to the treatment effect confirmation means and the environment safety monitoring means, wherein
the data storage/transmission means are connected by wireless with a host computer provided away from the ship,
the host computer monitors a state of the ballast water treatment system in advance before the ship reaches a port by using the control means based on treatment effect data and environment safety data received from the data storage/transmission means, maintains and manages operations of the ballast water treatment system to be proper, determines an amount of hypochlorite supplies to maintain the ballast water treatment system, and sends instructions for the amount of the supplies to the port for preparation work of the supplies to begin before the ship reaches the port,
the treatment effect confirmation means detects a state of a hypochlorite as an active substance of a bactericidal agent in ballast water when loading the ballast water, and
the environment safety monitoring means detects a state of the hypochlorite of the bactericidal agent remaining in ballast water when discharging the ballast water.

2. The remote monitoring device for the ballast water treatment system according to claim 1, wherein the treatment effect confirmation means is one or more kinds selected from a residual oxidant sensor, an ultraviolet sensor, an oxidizing-reducing potentiometer, a dissolved oxygen meter, a level meter of a bactericidal agent tank, a flowmeter of a bactericidal agent, and a flowmeter of an electrolytic device.

3. The remote monitoring device for the ballast water treatment system according to claim 2, wherein the environment safety monitoring means is one or more kinds selected from a residual oxidant sensor, an oxidizing-reducing potentiometer, a level meter of a bactericidal-agent neutralizer tank, and a flowmeter of a neutralizer.

4. The remote monitoring device for the ballast water treatment system according to claim 1, wherein the environment safety monitoring means is one or more kinds selected from a residual oxidant sensor, an oxidizing-reducing potentiometer, a level meter of a bactericidal-agent neutralizer tank, and a flowmeter of a neutralizer.

5. The remote monitoring device for the ballast water treatment system according to claim 1, wherein the hypochlorite of the bactericidal agent is an active chemical ingredient of the bactericidal agent.

6. The remote monitoring device for the ballast water treatment system according to claim 1, further comprising
a ballast tank that holds the ballast water and that is fluidly connected to a water intake port via a main line of the ship and a water discharge port via a discharge line of the ship,
a bactericidal agent storage tank that stores the bactericidal agent and that is fluidly connected to the main line at a first position located upstream of the ballast tank towards the water intake port of the ship, and
a neutralization storage tank that stores a neutralization agent that neutralizes the hypochlorite of the bactericidal agent and that is fluidly connected to the discharge line of the ship at a second position located downstream of the ballast tank towards the water discharge port of the ship.

7. The remote monitoring device for the ballast water treatment system according to claim 6, wherein
the host computer is configured to operate the control means to operate one or more valves in the ballast water treatment system to control the bactericidal agent storage tank and the neutralization storage tank in response to instructions received from the host computer via the data storage/transmission means.

8. A remote monitoring method for a ballast water treatment system provided to a ship, comprising:
transmitting treatment effect data and environment safety data obtained by a treatment effect confirmation means and an environment safety monitoring means provided to the ballast water treatment system to a data storage/transmission means;
wirelessly transmitting the data, via the data storage/transmission means, to a host computer provided away from the ship;
maintaining and managing operations of the ballast water treatment system to be proper, via the host computer, by monitoring from remote a state of the ballast water treatment system in advance before the ship reaches a port by using the control means based on treatment effect data and environment safety data received from the data storage/transmission means;
determining, via the host computer, an amount of hypochlorite supplies to maintain the ballast water treatment system; and
sending instructions for the amount of supplies to the port for preparation work of the supplies to begin before the ship reaches the port, wherein
the treatment effect confirmation means detects a state of a hypochlorite as an active substance of a bactericidal agent in ballast water when loading the ballast water; and
the environment safety monitoring means detects a state of the hypochlorite of a bactericidal agent remaining in ballast water when discharging the ballast water.

9. The remote monitoring method for a ballast water treatment system according to claim 8, wherein the hypochlorite of the bactericidal agent is an active chemical ingredient of the bactericidal agent.

10. The remote monitoring method for the ballast water treatment system according to claim 8, further comprising
operating, via the host computer, the control means to operate at least one or more valves in the ballast water treatment system to control the bactericidal agent storage tank and a neutralization storage tank in response to instructions received from the host computer via the data storage/transmission means.

11. A ballast water-treatment remote monitoring system comprising:
a treatment effect confirmation sensor installed on a ship that includes a ballast tank that detects a state of a hypochlorite as an active chemical ingredient of a bactericidal agent in ballast water during loading of the ballast water;
an environment safety monitoring sensor installed on the ship that includes the ballast tank that detects the state of the hypochlorite of the bactericidal agent in the ballast water during discharging of the ballast water;
a controller that is installed on the ship, that includes, or is communicatively connected to, a memory storage unit that electronically stores the state of the hypochlorite of the bactericidal agent detected by the treatment effect confirmation sensor and the environment safety monitoring sensor;
a transmitter and a receiver communicatively installed on the ship that includes the ballast tank that is communicatively connected to the controller and the memory storage and that transmits the state of the hypochlorite of the bactericidal agent detected by at least one of the treatment effect confirmation sensor and the environment safety monitoring sensor that is stored in the memory storage;
a host computer that is structurally detached from the ship, that is communicatively connected with the controller of the ship via the transmitter and the receiver of the ship, that remotely monitors and remotely manages the hypochlorite of the bactericidal agent within the ballast water in advance before the ship reaches a port, that receives treatment effect confirmation data and environmental safety data stored in the memory storage unit and detected by the treatment effect confirmation sensor and the safety monitoring sensor, respectively, from the transmitter of the ship, that determines an amount of supplies to maintain the ballast water treatment system, that transmits instructions for the amount of hypochlorite supplies to the port for preparation work of the supplies to begin before the ship reaches port, and that transmits to the ship preparation work instructions to the receiver of the ship prior to arriving at port in accordance with the state of the ballast water treatment system, wherein
the controller receives the preparation work instructions from the host computer and maintains or changes the state of the hypochlorite in the ballast storage tank of the ship prior to arriving at port to shorten a time period at port required to perform management of the ballast water.

12. The ballast water-treatment remote monitoring system according to claim 11, further comprising
a ballast tank that holds the ballast water and that is fluidly connected to a water intake port via a main line of the ship and a water discharge port via a discharge line of the ship,
a bactericidal agent storage tank that stores the bactericidal agent and that is fluidly connected to the main line at a first position located upstream of the ballast tank towards the water intake port of the ship, and
a neutralization storage tank that stores a neutralization agent that neutralizes the hypochlorite of the bactericidal agent and that is fluidly connected to the discharge line of the ship at a second position located downstream of the ballast tank towards the water discharge port of the ship.

13. The ballast water-treatment remote monitoring system according to claim 12, wherein
the host computer is configured to operate the controller to operate one or more valves in the ballast water treatment system to control the bactericidal agent storage tank and the neutralization storage tank in response to instructions received from the host computer via the receiver of the ship.

* * * * *